United States Patent [19]

Bergthaller

[11] Patent Number: 5,455,149
[45] Date of Patent: Oct. 3, 1995

[54] COLOR PHOTOGRAPHIC MATERIAL CONTAINING NOVEL YELLOW COUPLERS

[75] Inventor: Peter Bergthaller, Bergisch Gladbach, Germany

[73] Assignee: Agfa-Gevaert, AG, Leverkusen, Germany

[21] Appl. No.: 292,770

[22] Filed: Aug. 19, 1994

[30] Foreign Application Priority Data

Sep. 1, 1993 [DE] Germany .......................... 43 29 418.9

[51] Int. Cl.⁶ .................................................. G03C 1/46
[52] U.S. Cl. ........................ 430/503; 430/389; 430/543; 430/553; 430/557; 430/558
[58] Field of Search .................................. 430/503, 557, 430/558, 553, 543, 389

[56] References Cited

U.S. PATENT DOCUMENTS

| | | | |
|---|---|---|---|
| 4,870,000 | 9/1989 | Bergthaller et al. | 430/557 |
| 5,021,330 | 6/1991 | Bergthaller et al. | 430/557 |
| 5,021,332 | 6/1991 | Bergthaller et al. | 430/557 |

FOREIGN PATENT DOCUMENTS

| | | |
|---|---|---|
| 0346899 | 12/1989 | European Pat. Off. . |
| 2433812 | 2/1975 | Germany . |
| 4014936 | 11/1991 | Germany . |

*Primary Examiner*—Charles L. Bowers, Jr.
*Assistant Examiner*—Geraldine Letscher
*Attorney, Agent, or Firm*—Connolly & Hutz

[57] ABSTRACT

Yellow azomethine dyes of particularly elevated stability are obtained from yellow couplers of the formula I by chromogenic development

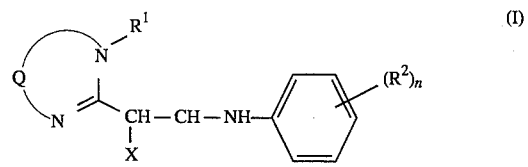

In formula I
Q means a residue to complete a 4-pyrimidone ring;
X means a residue which is eliminable on chromogenic development;
$R^1$ means alkyl with 1 to 6 C atoms;
$R^2$ means halogen, —$CF_3$, alkyl, aryl, alkoxy, aryloxy, alkylthio, arylthio, acylamino, sulphonamido, sulphuramido, carbamoyl, alkoxycarbonyl, sulphonyl, sulphamoyl or a heterocyclic residue, wherein two adjacent residues $R^2$ may complete a ring;
n means an integer from 1 to 4.

4 Claims, No Drawings

COLOR PHOTOGRAPHIC MATERIAL CONTAINING NOVEL YELLOW COUPLERS

The present invention provides novel yellow couplers for colour photographic recording materials and colour photographic recording materials containing the novel yellow couplers. The present invention also provides images containing yellow azomethine dyes of particularly high stability formed from the novel yellow couplers.

The novel yellow couplers are of the general formula I

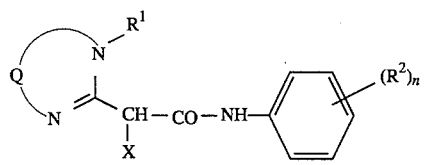

in which

Q means a residue to complete a 4-pyrimidone ring;

X means a residue which is eliminable on chromogenic development;

$R^1$ means alkyl with 1 to 6 C atoms;

$R^2$ means halogen, —$CF_3$, alkyl, aryl, alkoxy, aryloxy, alkylthio, arylthio, acylamino, sulphonamido, sulphuramido, carbamoyl, alkoxycarbonyl, sulphonyl, sulphamoyl or a heterocyclic residue, wherein two adjacent residues $R^2$ may complete a ring;

n means an integer from 1 to 4.

The residue represented by Q to complete a 4-pyrimidone ring is in particular a group of the formula

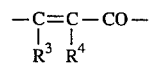

which $R^3$ and $R^4$ mean a residue to complete a 5- to 7-membered ring, for example a benzene, pyrazole or cyclohexene ring, or in which one of the residues $R^3$ and $R^4$ denotes hydrogen, alkyl, aryl or alkoxy, the other —CN, acylamino, carbamoyl, alkoxycarbonyl, sulphonyl or a phosphorus ester group.

The residue represented by X which is eliminable on chromogenic development is, for example, a halogen atom, in particular —Cl, or a cyclic group attached via an oxygen atom or a ring nitrogen atom. In particularly preferred embodiments of the invention, X means a 1,2,3- or 1,2,4-triazole residue.

An alkyl residue represented by $R^1$ or $R^2$ or contained in a substituent represented by $R^2$ may be straight-chain or branched, unsubstituted or substituted. Possible substituents are, for example, —OH, alkoxy or aryloxy.

It is preferred if at least one of the substituents represented by $R^2$, $R^3$ and $R^4$ or a substituent on a ring completed by $R^3$ and $R^4$ is a relatively long chain residue with a diffusion-inhibiting action or is attached to a polymer backbone.

Examples of couplers according to the invention are shown below.

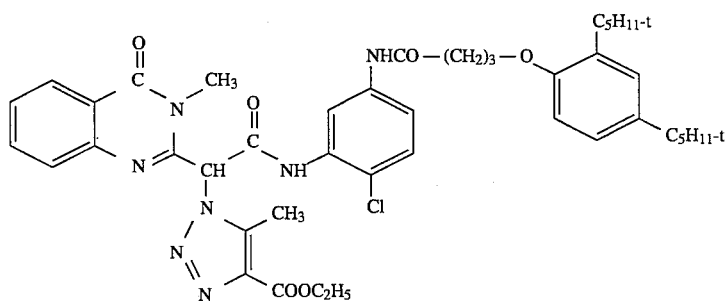

(1)

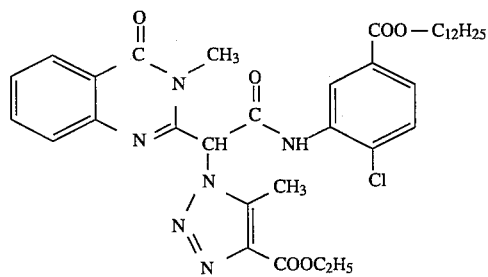

(2)

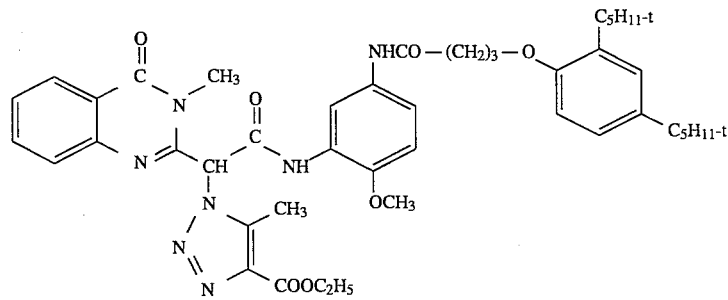

(3)

-continued
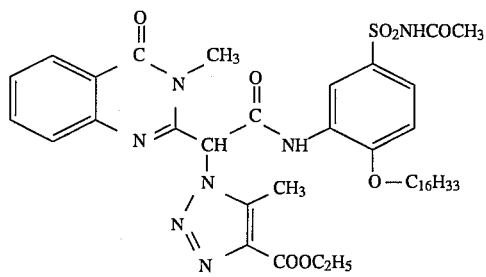
(4)
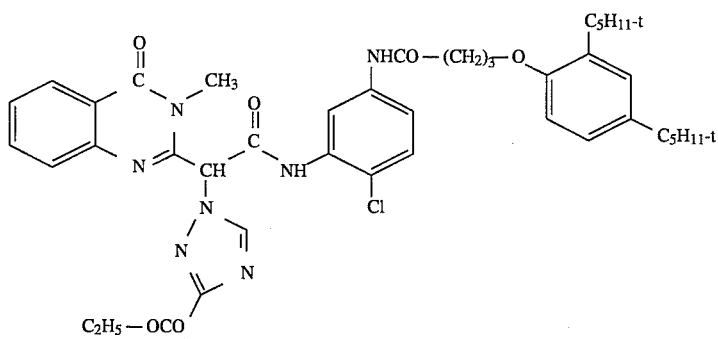
(5)
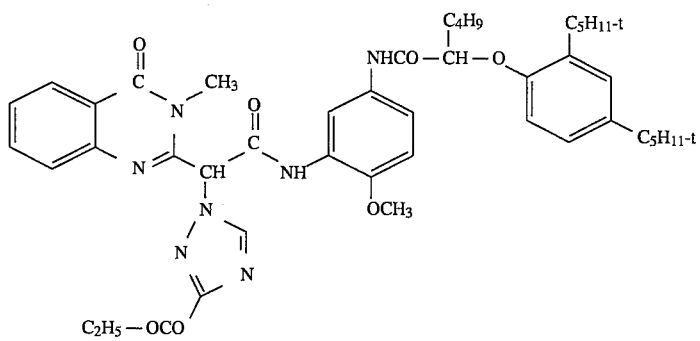
(6)
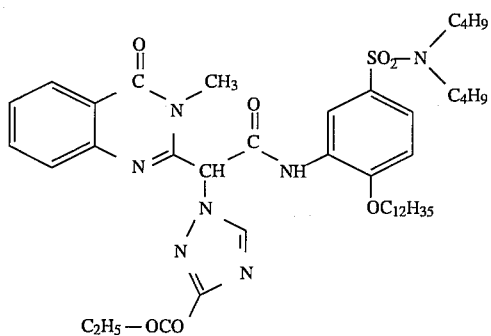
(7)
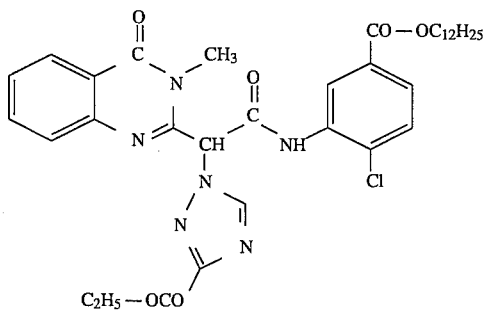
(8)

-continued
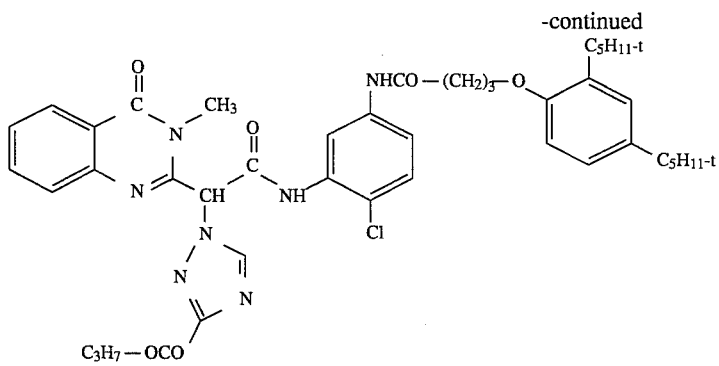 (9)
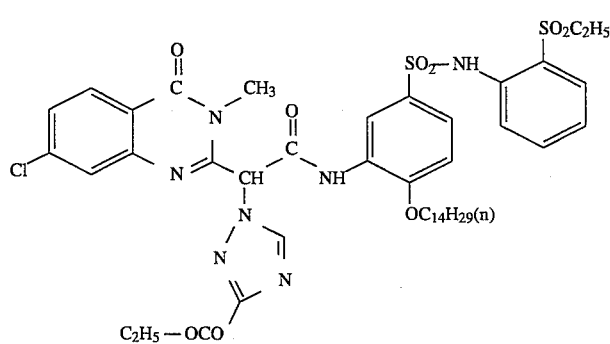 (10)
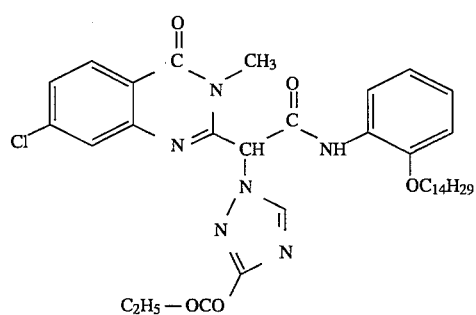 (11)
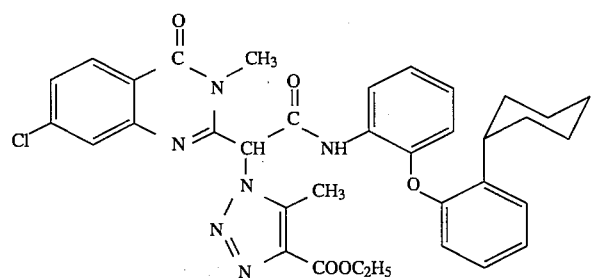 (12)
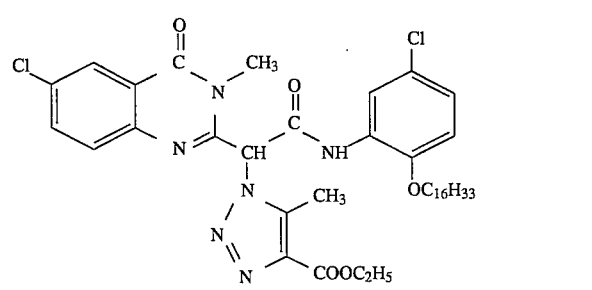 (13)

-continued
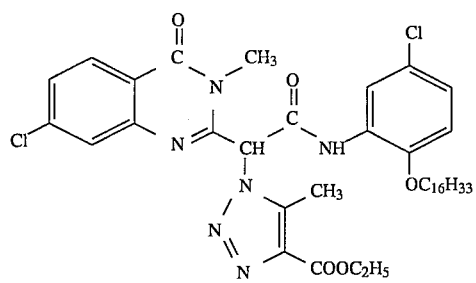
(14)
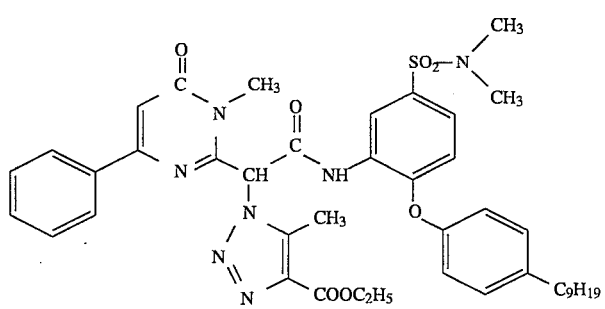
(15)
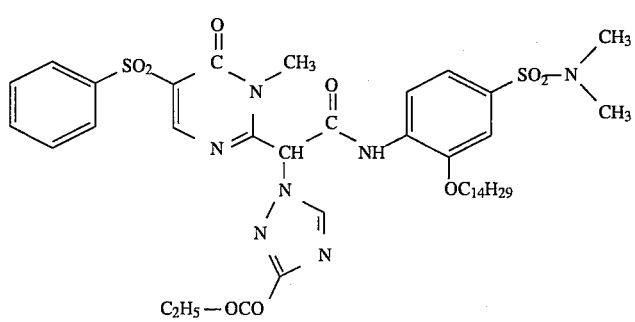
(16)
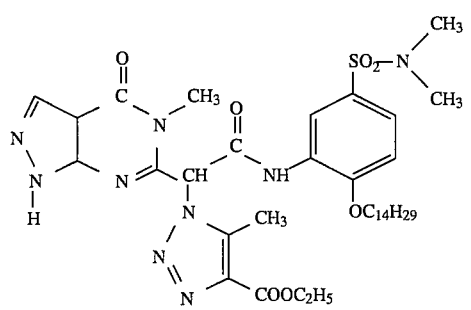
(17)
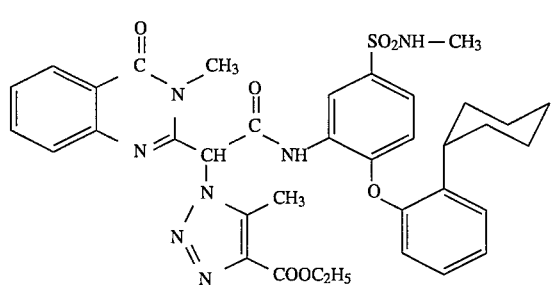
(18)

-continued
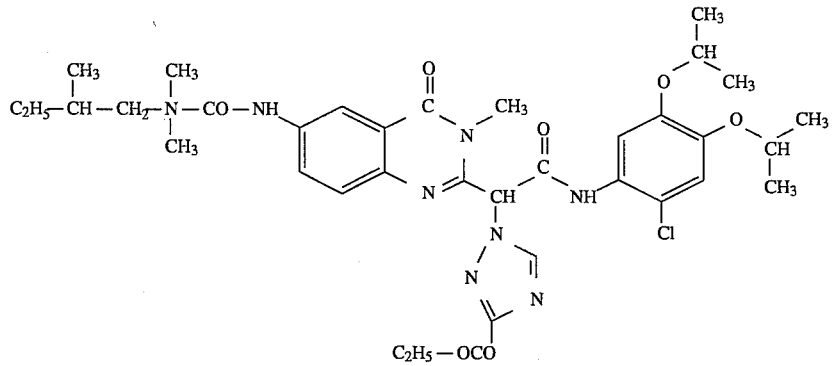 (19)
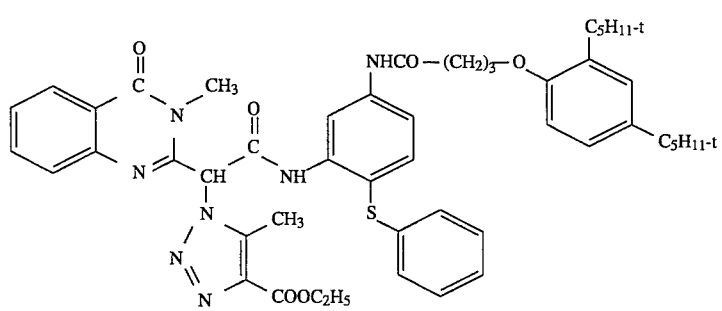 (20)
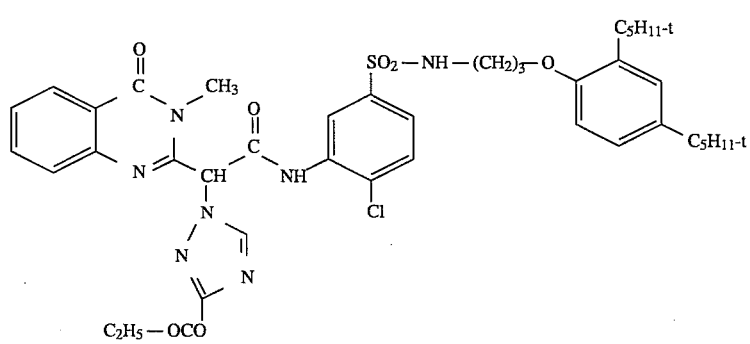 (21)
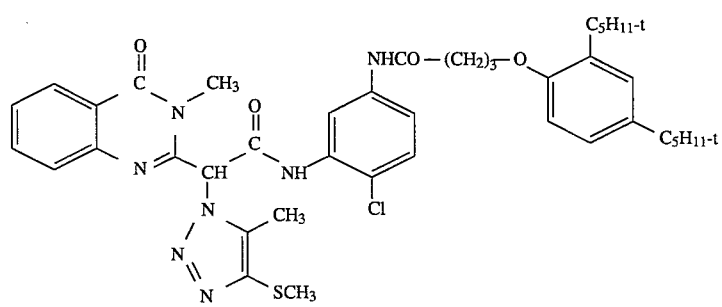 (22)
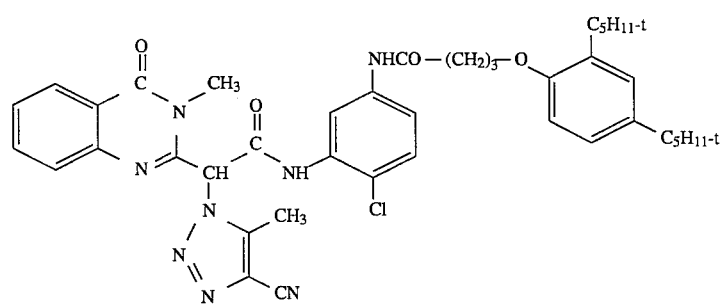 (23)

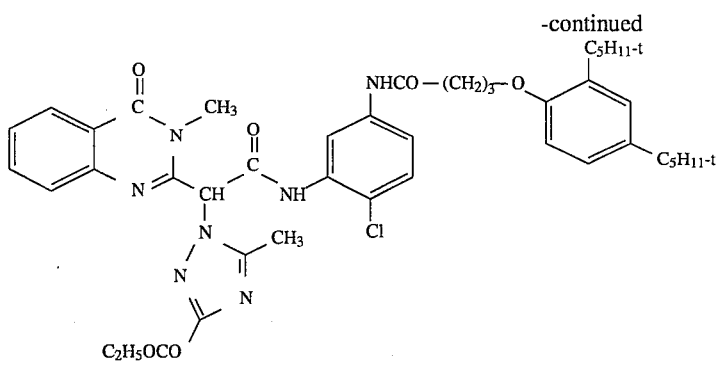
(24)
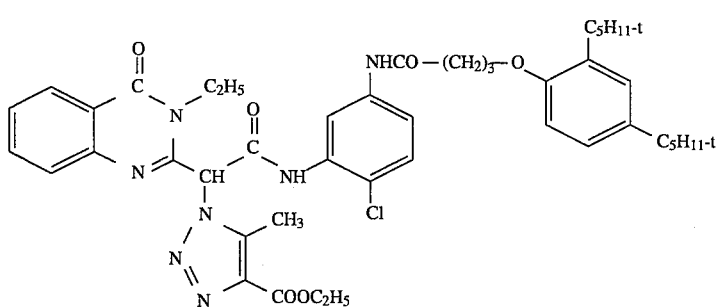
(25)
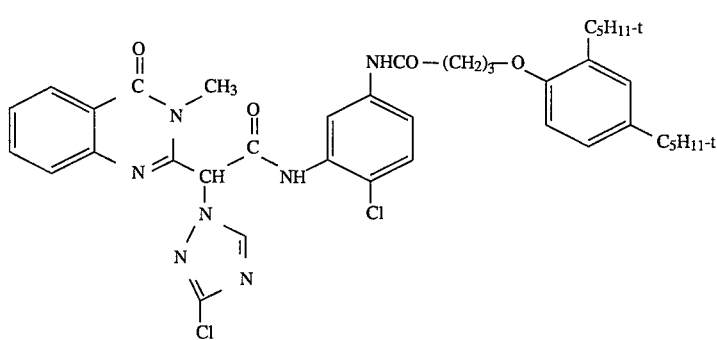
(26)
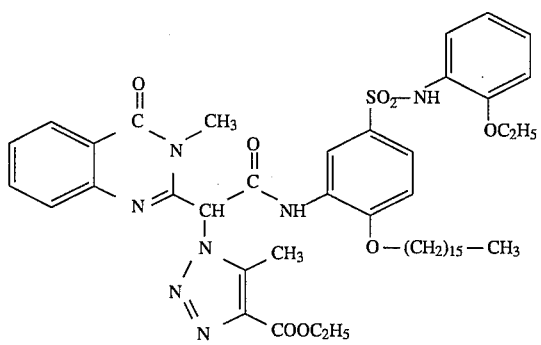
(27)
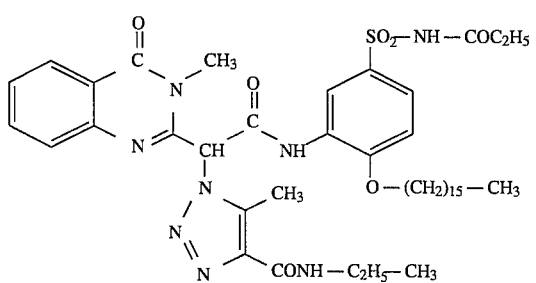
(28)

-continued
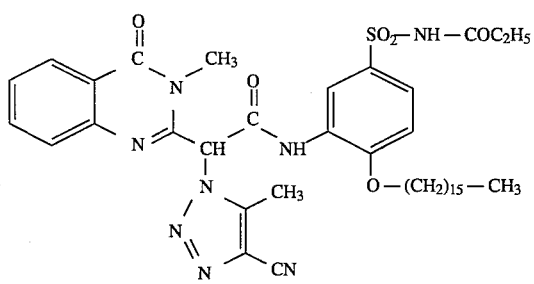
(29)
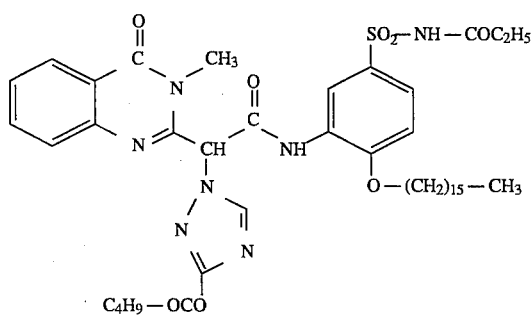
(30)
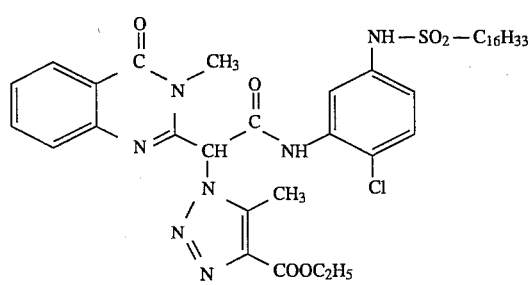
(31)
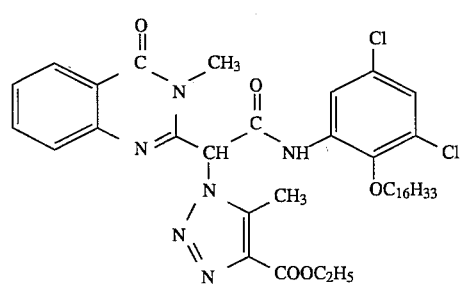
(32)
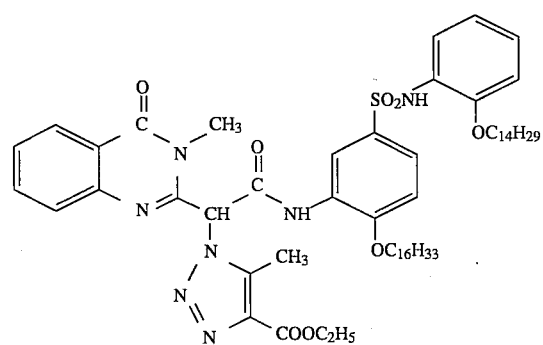
(33)

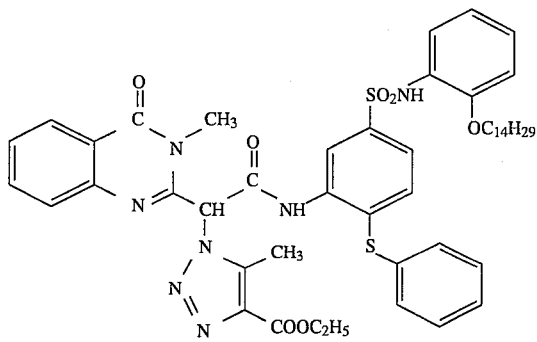

(34)

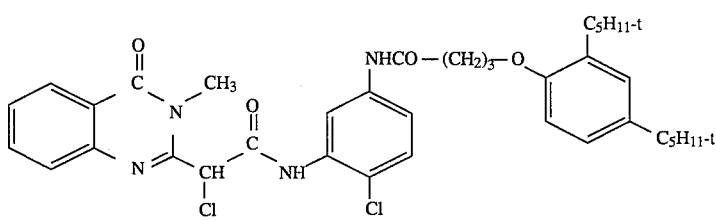

(35)

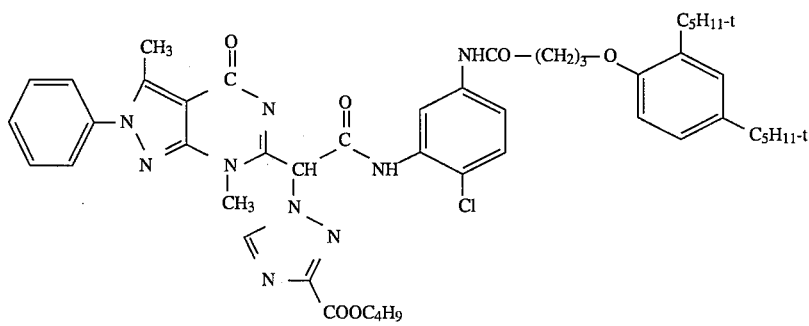

(36)

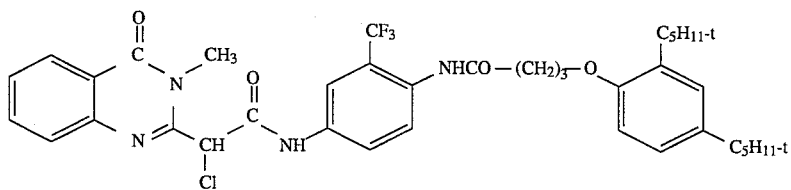

(37)

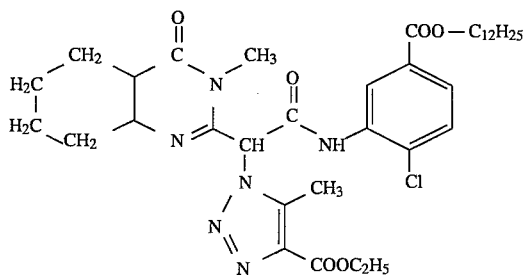

(38)

Production of the novel yellow couplers may be particularly simply represented by the example of 3-alkylquinazolone 2-acetic acid anilides.

2-Aminobenzoic acid N-methylamide (anthranilic acid methylamide) is prepared by reacting isatoic anhydride (1-H-benzoxazine-2,4-dione) with an aqueous methylamine solution.

The quinazolone 2-acetic acid derivative is produced from substituted 2-aminobenzamides, for example, by reaction with a malonimino ether hydrochloride, which is obtained from the corresponding cyanoacetic acid ester or cyanoacetic acid anilide with HCl and ethanol at 0° C., or with a malonanilide-imino thioether. In the case of the N-alkylated quinazolone acetic ester, introduction of the anilide group may proceed particularly simply by melting at temperatures of between 145 and 170° C. The process is entirely customary in yellow coupler chemistry and is precisely described in DE-A-37 11 418. Chlorobenzene is a preferred solvent for this purpose.

Nucleophilic fugitive groups are generally introduced by substituting a good starting group, for example a chlorine or bromine atom or a selenium oxide group, with the corresponding nucleophile, preferably in the presence of an auxiliary base.

The following examples are intended to elucidate the general instructions for the production of the novel yellow couplers.

3-methylquinazolin-4-one 2-acetic acid ethyl ester:

42 g (0.215 mol) of malonic acid ethyl ester imino ethyl ether hydrochloride are added in three portions to a stirred solution, heated to 80° C., of 30 g (0.2 mol) of anthranilic acid methylamide in 150 ml of isopropanol and the mixture is refluxed for a further 40 minutes. The mixture is then poured over 300 g of ice, left to stand for 1 hour and suction filtered. Yield: 50 g of white needles of melting point 105°–107° C.

3-methylquinazolin-4-one 2-acetic acid 2-chloro-5-[4 (2,4-di-t-pentylphenoxy)butyryl]aminoanilide (4-equivalent coupler).

24 g of 3-methylquinazolin-4-one 2-acetic acid ethyl ester and 45 g of 2-chloro-5-[4(2,4-di-t-pentylphenoxy)butyryl]-aminoanilide in 50 ml of 1,2-dichlorobenzene are heated to 155° C. for 90 minutes and the liberated ethanol is stripped out with a weak stream of nitrogen. The mixture is then poured into 250 ml of acetonitrile and left to crystallise for 5 days. The mixture is suction filtered, the crystals washed with acetonitrile and dried in air. Yield: 36 g, melting point 173°–177° C.

3-methylquinazolin-4-one 2-bromoacetic acid 2-chloro-5-[4(2,4-di-t-pentylphenoxy)butyryl]-aminoanilide (brominated coupler).

30 g of 4-equivalent coupler are heated to 95° C. in 200 ml of acetic acid, the mixture is rapidly cooled to 35° C. and 8 g of bromine in 30 ml of acetic acid are added dropwise while the mixture is vigorously stirred. Stirring is continued for a further 15 minutes and the brominated coupler is precipitated with 45 g of ice. The mixture is decanted, the precipitate washed with copious water and digested with 100 ml of acetonitrile. Yield: 29 g, melting point 200°–204° C.

Coupler 1 according to the invention:

7 g of the brominated coupler are dissolved in 100 ml of ethyl acetate, 3 g of 4-methyl-1,2,3-triazole-5-carboxylic acid ethyl ester are added and 3 ml of tetramethylguanidine are added dropwise at 25° C. The mixture is stirred for a further hour, 40 ml of 10% hydrochloric acid are added, the aqueous phase is separated, the organic phase is washed with water, dried with magnesium sulphate, evaporated under a water-jet vacuum, digested with hexane and recrystallised from acetonitrile. Coupler 1 according to the invention is obtained as a mixture of two isomers with a melting range of 145°–155° C. Yield: 5 g.

The novel couplers have excellent stability and have no tendency to decompose by acid cleavage, which often leads to a loss of activity, particularly with benzoylacetanilides.

The couplers yield yellow dyes with excellent stability, particularly against hydrolytic degradation by "dark fading". They are thus excellently suited to the production of photographic transparencies or negatives and for prints.

Using the novel couplers, it is possible to produce photographic print materials in which, in contrast with the prior art, the blue-sensitive layer is the uppermost light sensitive layer. The UV absorption of the residual coupler, which is often considerable, may thus contribute to the protection of the underlying magenta and cyan partial images against UV irradiation.

The yellow dyes formed from the novel couplers generally exhibit absorption maxima at approximately 450 nm, which are at a longer wavelength than the yellow dyes formed from comparable pivaloylacetanilides. Visually, however, the yellow dyes do not appear redder, because the long-wave side of their absorption band falls away extraordinarily steeply. Thus, even at high densities, they exhibit no shift towards clayey or orange tones.

The novel yellow couplers have excellent solubility in customary coupler solutions, for example high-boiling esters or carbonamides or phosphoric acid esters and, even at a high coupler/oil former ratio, form stable crystallisation-resistant dispersions or emulsions. The novel yellow couplers may also be used in the form of filled latices or dispersions containing no oil formers.

In order to achieve defined coupling kinetics, the novel yellow couplers may be used blended with known yellow couplers without any disadvantages.

One class of compounds which is preferred according to the invention, the quinazolone 2-acetic acid anilides, is based on a structure which, in its non-alkylated form (in the quinazolone ring), is, however, already known from DE-A 37 11 418. However, the compounds stated therein do not generally produce attractive yellow dyes on chromogenic development, but are very well suited as functional couplers suitable for releasing photographically useful groups, in particular as DIR couplers.

It is surprising that alkylation of a single N atom is sufficient to shift the absorption of the azomethine dye to shorter wavelengths, so producing clear yellow tones which have neither a green nor red cast. The substitution of the fused benzene ring with one of the other stated groups, for example a pyrazole or imidazole group may, however, bring about an increase or decrease in the extinction coefficients or an insignificant shift in tone.

Examples of colour photographic materials are in particular colour negative films, colour reversal films and colour photographic papers.

Suitable supports for the production of colour photographic materials are, for example, films and sheets of semi-synthetic and synthetic polymers, such as cellulose nitrate, cellulose acetate, cellulose butyrate, polystyrene, polyvinyl chloride, polyethylene terephthalate and polycarbonate and paper laminated with a barytes layer or an α-olefin polymer layer (for example polyethylene). These supports may be coloured with dyes and pigments, for example titanium dioxide. The surface of the support is generally subjected to a treatment in order to improve the adhesion of the photographic emulsion layer, for example to a corona discharge with subsequent application of a substrate layer. A light-reflective support is preferred according to the invention.

The photographic emulsion layers substantially comprise binders, silver halide grains and colour couplers.

Gelatine is preferably used as the binder. Gelatine may, however, be entirely or partially replaced with other synthetic, semi-synthetic or also naturally occurring polymers.

As a rule, the binders have a sufficient quantity of functional groups available so that satisfactorily resistant layers may be produced by reaction with suitable hardeners. Such functional groups are in particular amino groups, but also carboxyl groups, hydroxyl groups and active methylene groups.

The silver halide present in the photographic material as the photosensitive constituent may contain chloride, bromide or iodide or mixtures thereof as the halide. For example, the halide content of at least one layer may consist of 0 to 15 mol % iodide, 0 to 100 mol % chloride and 0 to 100 mol % bromide. In the case of colour negative and colour reversal films, silver bromide-iodide emulsions are customarily used, in the case of colour negative and colour reversal paper silver chloride-bromide emulsions with a high chloride content up to pure silver chloride emulsions are customarily used. Silver halide emulsions, the halide content of which consists of up to 95 mol. % or more of chloride, preferably up to 99 mol. % or more, are preferred according to the invention. The crystals may be predominantly compact, for example regularly cubic or octahedral, or they may have transitional shapes. Preferably, however, lamellar crystals may also be present, the average ratio of diameter to thickness of which is preferably at least 5:1, wherein the diameter of a grain is defined as the diameter of a circle the contents of which correspond to the projected surface area of the grain. The layers may, however, also have tabular silver halide crystals in which the ratio of diameter to thickness is substantially greater than 5:1, for example 12:1 to 30:1.

The silver halide grains may also have a multi-layered grain structure, in the simplest case with one internal zone and one external zone of the grain (core/shell), wherein the halide composition and/or other modifications, such as for example doping, of the individual grain zones are different. The average grain size of the emulsions is preferably between 0.2 µm and 2.0 µm, the grain size distribution may be both homodisperse and heterodisperse. A homodisperse grain size distribution means that 95% of the grains do not deviate by more than ±30% from the average grain size.

Two or more types of silver halide emulsions which are produced separately may be used as a mixture.

The emulsions may be chemically or spectrally sensitised in the customary manner and the emulsion layers, together with other non-photosensitive layers, may be hardened in the customary manner with known hardeners, in particular with hardeners which activate carboxyl groups, such as carbamoylpyridinium salts (for example according to DE-A 22 25 230, DE-A-23 17 677, DE-A-24 39 551).

Colour photographic silver halide materials customarily contain at least one silver halide layer to record the light from each of the three ranges of the spectrum red, green and blue. To this end, the photographic emulsions may be spectrally sensitised by using methine dyes or other dyes. Particularly suitable dyes are cyanine dyes, merocyanine dyes and complex merocyanine dyes.

A review of the polymethine dyes suitable as spectral sensitisers, suitable combinations of the dyes and the combinations with supersensitising effects is contained in *Research Disclosure* 17643 (December 1978), section IV.

In particular, the following dyes—classified by spectral range—are suitable:

1. as red sensitisers 9-ethylcarbocyanines with benzothiazole, benzoselenazole or naphthothiazole as basic terminal groups, which may be substituted in 5th or 6th position by halogen, methyl, methoxy, carbalkoxy, aryl, together with 9-ethyl-naphthoxathia- or -selenocarbocyanines and 9-ethyl-naphthothiaoxa- or -benzoimidazocarbocyanines, provided that the dyes bear at least one sulphoalkyl group on the heterocyclic nitrogen.

2. as green sensitisers 9-ethylcarbocyanines with benzoxazole, naphthoxazole or a benzoxazole and a benzothiazole as basic terminal groups, together with benzimidazolecarbocyanines, which may also be further substituted and must also contain at least one sulphoalkyl group on the heterocyclic nitrogen.

3. as blue sensitisers symmetrical or asymmetrical benzimidiazo-, oxa-, thia- or selenocyanines with at least one sulphoalkyl group on the heterocyclic nitrogen and optionally further substituents on the aromatic ring, together with apomerocyanines with a rhodanine group.

Sensitisers may be dispensed with if the intrinsic sensitivity of the silver halide is adequate for a specific range of the spectrum, for example the blue sensitivity of silver bromides.

The differently sensitised emulsion layers are associated with non-diffusing low molecular weight or polymeric colour couplers which may be located in the same layer or in an adjacent layer. Usually, cyan couplers are associated with the red-sensitive layers, magenta couplers with the green-sensitive layers and yellow couplers with the blue-sensitive layers. In the present case, a yellow coupler of the formula I is associated with the blue-sensitive layer or layers.

Colour couplers to produce the cyan partial colour image are generally couplers of the phenol or α-naphthol type; suitable examples of these are (formulae II, III, IV, V, VI)

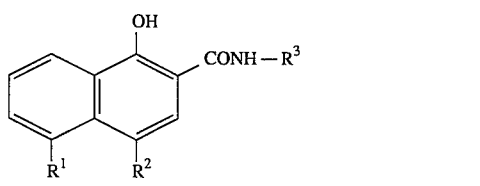

(II)

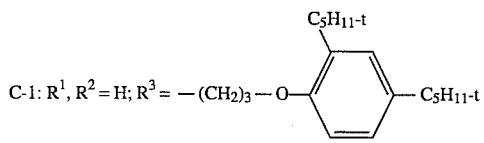

C-2: $R^1 = -NHCOOCH_2-CH(CH_3)_2$; $R^2 = H$;
$R^3 = -(CH_2)_3-OC_{12}H_{25}$

C-3: $R^1 = H$; $R^2 = -OCH_2-CH_2-SO_2CH_3$; $R^3 = -C_{16}H_{33}$

C-4: $R^1 = H$; $R^2 = -OCH_2-CONH-(CH_2)_2-OCH_3$;

-continued

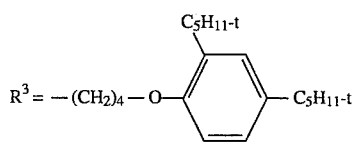

C-5: $R^1, R^2 = H$; 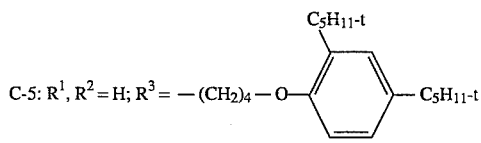

C-6: $R^1, R^2 = H$; 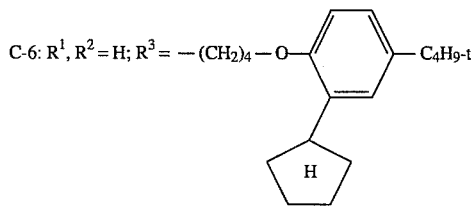

C-7: $R^1 = H$; $R^2 = Cl$; $R^3 = -C(C_2H_5)_2 - C_{21}H_{43}$

C-8: $R^1 = H$; $R^2 = -O-CH_2-CH_2-S-CH(COOH)-C_{12}H_{25}$;
$R^3$ = cyclohexyl

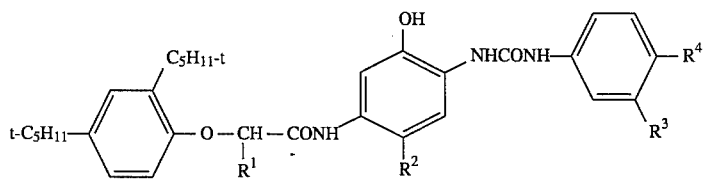 (III)

C-9: $R^1 = -C_4H_9$; $R^2 = H$; $R^3 = -CN$; $R^4 = Cl$

C-10: $R^1 = -C_4H_9$; $R^2 = H$; $R^3 = H$; $R^4 = -SO_2-CHF$

C-11: $R^1 = -C_4H_9$; $R^2 = $ 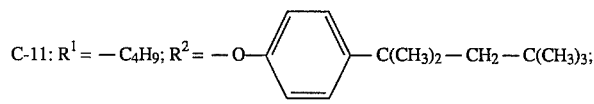

$R^3 = H$; $R^4 = H$

C-12: $R^1 = C_2H_5$; $R^2, R^3 = H$; $R^4 = -SO_2CH_3$

C-13: $R^1 = -C_4H_9$; $R^2, R^3 = H$; $R^4 = -SO_2-C_4H_9$

C-14: $R^1 = -C_4H_9$; $R^2 = H$; $R^3 = -CN$; $R^4 = -CN$

C-15: $R^1 = -C_4H_9$; $R^2, R^3 = H$; $R^4 = -SO_2-CH_2-CHF_2$

C-16: $R^1 = -C_2H_5$; $R^2, R^3 = H$; $R^4 = -SO_2CH_2-CHF-C_3H_7$

C-17: $R^1 = -C_4H_9$; $R^2, R^3 = H$; $R^4 = F$

C-18: $R^1 = -C_4H_9$; $R^2, R^3 = H$; $R^4 = -SO_2CH_3$

C-19: $R^1 = -C_4H_9$; $R^2, R^3 = H$; $R^4 = -CN$

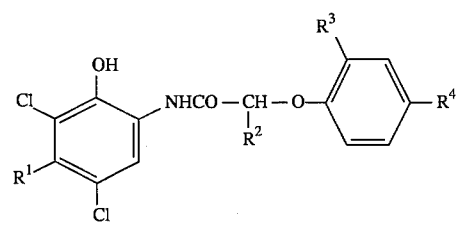 (IV)

C-20: $R^1 = -CH_3$; $R^2 = -C_2H_5$; $R^3, R^4 = -C_5H_{11}$-t

C-21: $R^1 = -CH_3$; $R^2 = H$; $R^3, R^4 = -C_5H_{11}$-t

C-22: $R^1, R^2 = -C_2H_5$; $R^3, R^4 = -C_5H_{11}$-t

C-23: $R^1 = -C_2H_5$; $R^2 = -C_4H_9$; $R^3, R^4 = -C_5H_{11}$-t

C-24: $R^1 = -C_2H_5$; $R^1 = -C_4H_9$; $R^3, R^4 = -C_4H_9$-t

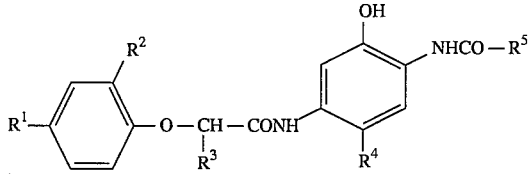

(V)

C-25: $R^1, R^2 = -C_5H_{11}$-t; $R^3 = -C_4H_9$; $R^4 = H$; $R^5 = -C_3H_7$

C-26: $R^1 = -NHSO_2-C_4H_9$; $R^2 = H$; $R^3 = -C_{12}H_{25}$; $R^4 = Cl$; $R^5 = $ Phenyl C-27: $R^1, R^2 = -C_5H_{11}$-t; $R^3 = -C_3H_7$-i; $R^4 = Cl$; $R^5 = $ Pentafluorophenyl C-28: $R^1 = -C_5H_{11}$-t; $R^2 = Cl$; $R^3 = -C_6H_{13}$; $R^4 = Cl$; $R^5 = $ -2-Chlorophenyl In preferred embodiments of the invention, the phenolic cyan couplers used to produce the cyan partial colour image are those which bear a ballasted acylamino residue in 2nd position and an ethyl group in 5th position, for example couplers of the formula IV, in which $R^1$ means ethyl and $R^2$, $R^3$ and $R^4$ mean alkyl.

Colour couplers to produce the magenta partial colour image are generally couplers of the 5-pyrazolone, indazolone or pyrazoloazole type; suitable examples of these are

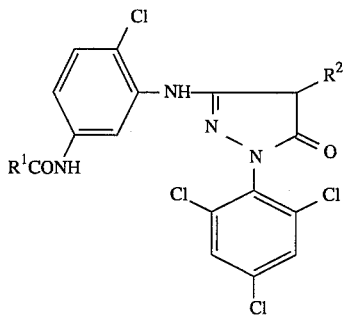

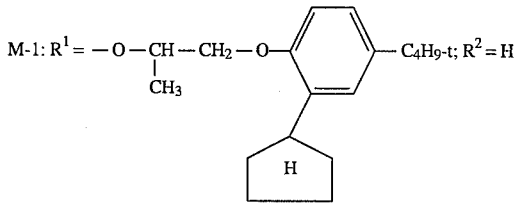

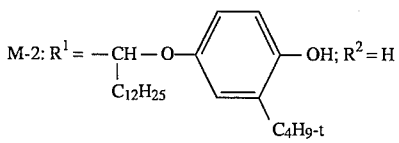

M-3: $R^1 = -C_{13}H_{27}$; $R^2 = H$

M-4: $R^1 = -CO_{16}H_{33}$; $R^2 = H$

-continued
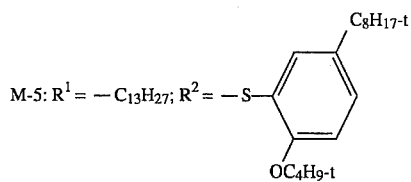
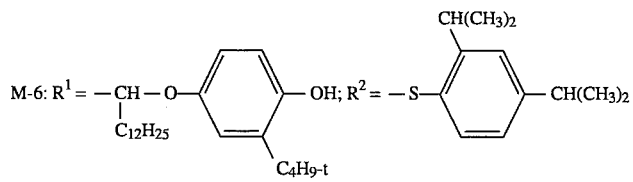
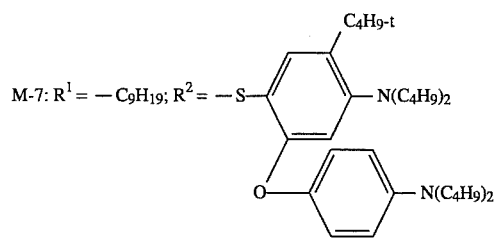
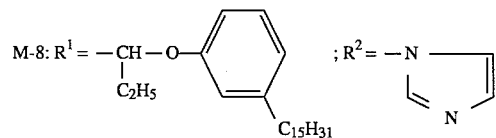
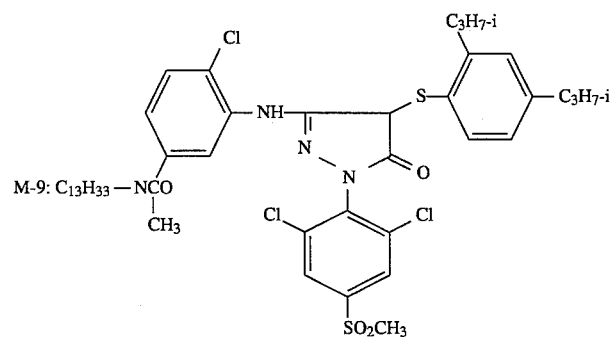
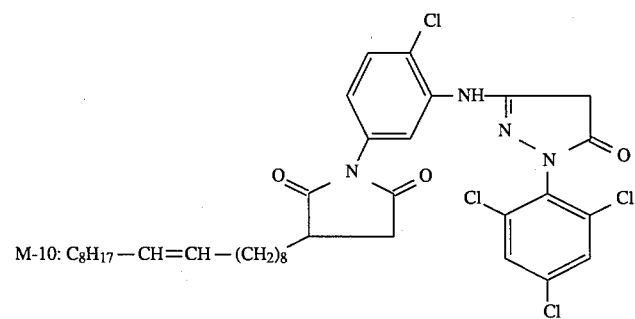

-continued
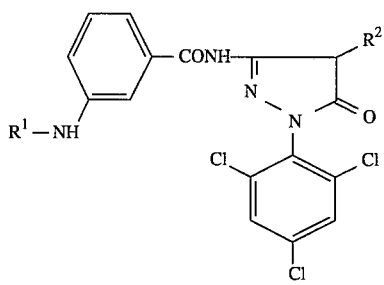
M-11: $R^1 = -SO_2-\text{C}_6\text{H}_4-OC_{12}H_{25}$; $R^2 = H$
M-12: $R^1 = -CO-CH_2-O-\text{Ar}$ (2-$C_5H_{11}$-t, 4-$C_5H_{11}$-t); $R^2 = H$
M-13: $R^1 = -CO-CH(C_2H_5)-O-\text{Ar}$ (2-$C_5H_{11}$-t, 4-$C_5H_{11}$-t); $R^2 = H$
M-14: $R^1 = -CO-CH(C_2H_5)-O-\text{Ar}$ (2-$C_5H_{11}$-t, 4-$C_5H_{11}$-t);
$R^2 = -O-\text{C}_6\text{H}_4-COOC_2H_5$
M-15: $C_{17}H_{35}CONH$— pyrazolone with N-aryl (4-substituted phenyl bearing $SO_3H$ and $O$-phenyl)
M-16: $C_{15}H_{31}$— (3-pentadecylphenoxy)-CH($C_2H_5$)-CONH— pyrazolone with N-(2-chloro-4,6-dimethylphenyl)

M-17:
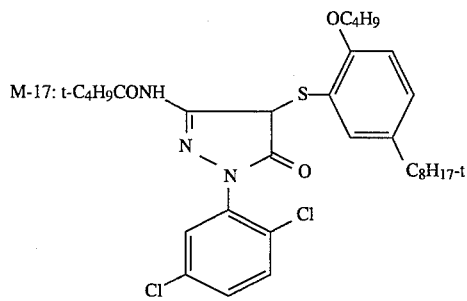
(VIa)
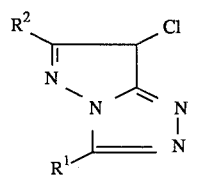
M-18: $R^1 = -(CH_2)_3-$ 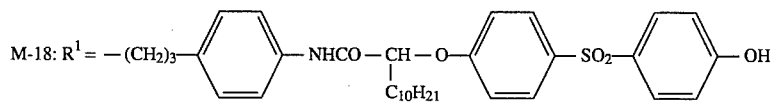
$R^2 = -CH_3$
M-19: $-(CH_2)_3-$ 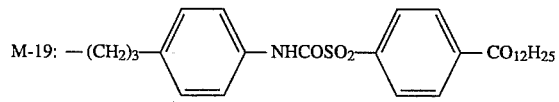
$R^2 = CH_3$
M-20: $R^1 = $ 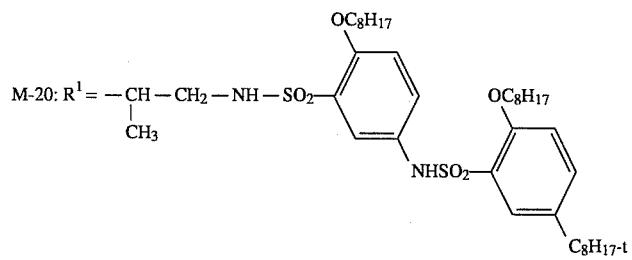
$R^2 = -C_4H_9\text{-}t$
M-21
$R^1 = -(CH_2)_3-$ 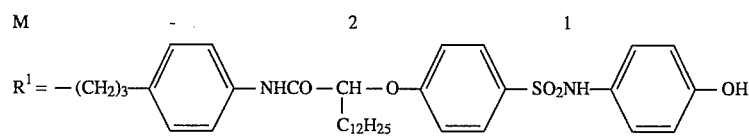
$R^2 = -CH_3$
M-22: $R^1 = -(CH_2)_3-$ 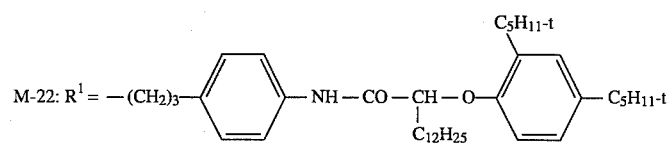
$R^2 = -CH_3$
M-23: $R^1 = $ 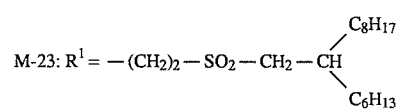
$R^2 = -CH_3$ -continued
M-24: R¹ = 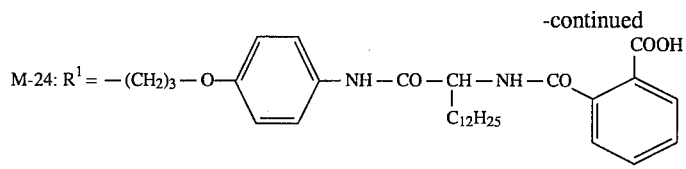
R² = —CH₃
(VIIa)
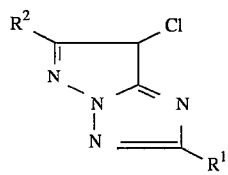
M-25: R¹ = 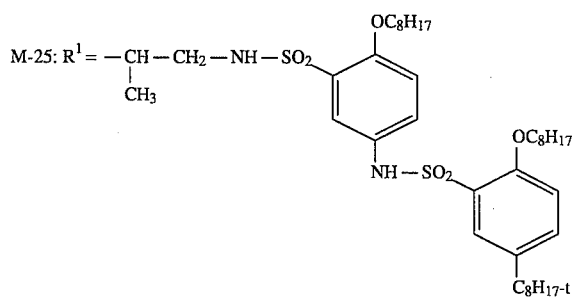
R² = —CH₃
M-26: R¹ = 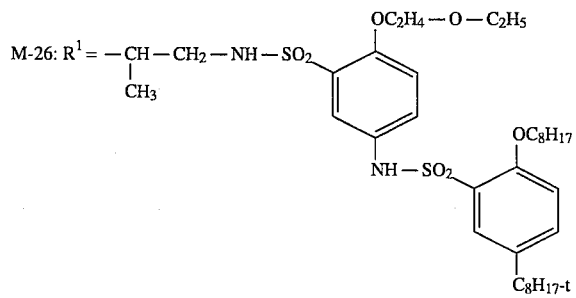
R² = —CH₃
M-27: R¹ = 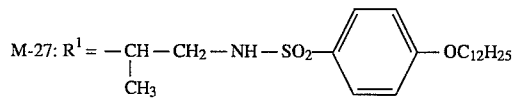
R² = —C₃H₇-i
M-28: R¹ = 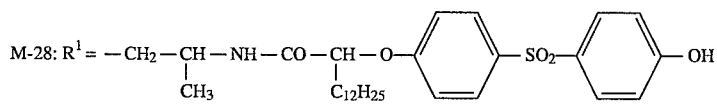
R² = —CH₃
M-29: R¹ = —C₃H₇-i
R² = 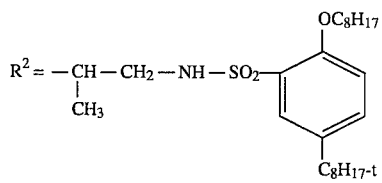

-continued

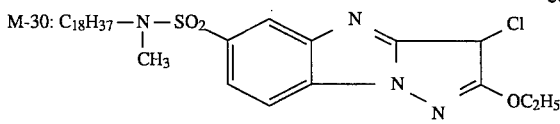

Pyrazoloazole couplers of the general formulae VI and VII

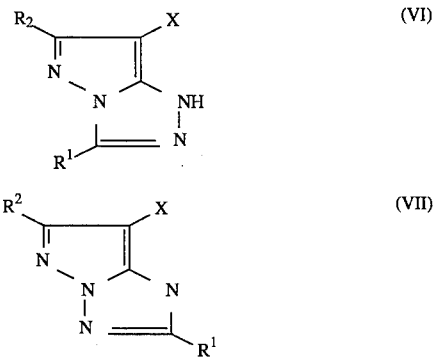

are described, for example, in U.S. Pat. Nos. 3,725,067 and 4,540,654. In the formulae VI and VII:

X means H or a group which may be released under the conditions of colour development;

$R^1$, $R^2$ mean H alkyl aralkyl aryl alkoxy, aroxy alkylthio, arylthio, amino, anilino, acylamino, cyano, alkoxycarbonyl, carbamoyl, sulphamoyl, wherein these residues may be further substituted.

In particularly preferred embodiments of the invention, pyrazoloazole couplers of one of the formulae VI and VII, in which $R^2$ means a tertiary alkyl, are used to produce the magenta partial colour image.

The colour couplers may be 4-equivalent couplers, but they may also be 2-equivalent couplers. The latter are derived from 4-equivalent couplers by containing a substituent at the coupling site which is eliminated on coupling. 2-equivalent couplers are considered to be those which are colourless, as well as those which have an intense intrinsic colour which on colour coupling disappears or is replaced by the colour of the image dye produced (mask couplers), and also white couplers which, on reaction with colour developer oxidation products, give rise to substantially colourless products. 2-equivalent couplers are further considered to be those which contain an eliminable residue at the coupling site, which residue is liberated on reaction with colour developer oxidation products and so either directly or after one or more further groups are eliminated from the initially eliminated residue (for example, DE-A-27 03 145, DE-A-28 55 697, DE-A-31 05 026, DE-A-33 19 428), produces a specific desired photographic effect, for example as a development inhibitor or accelerator. Examples of such 2-equivalent couplers are the known DIR couplers as well as DAR or FAR couplers.

DIR couplers, which release azole type development inhibitors, for example triazoles and benzotriazoles, are described in DE-A-24 14 006, 26 10 546, 26 59 417, 27 54 281, 28 42 063, 36 26 219, 36 30 564, 36 36 824, 6 44 416. Further advantages for colour reproduction, i.e. colour separation and colour purity, and for the reproduction of detail, i.e. sharpness and graininess, are to be achieved with such DIR couplers, which, for example, do not release the development inhibitor immediately as a consequence of coupling with an oxidised colour developer, but instead only after a further subsequent reaction, which is, for example, achieved with a time control group. Examples of this are described in DE-A-28 55 697, 32 99 671, 38 18 231, 35 18 797, in EP-A-0 157 146 and 0 204 175, in U.S. Pat. Nos. 4,146,396 and 4,438,393 and in GB-A-2,072,363.

In order to increase sensitivity, contrast and maximum density, principally DAR or FAR couplers may be used which eliminate a development accelerator or fogging agent. Compounds of this type are described, for example, in DE-A-25 34 466, 32 09 110, 33 33 355, 34 10 616, 34 29 545, 34 41 823, in EP-A-0 089 834, 0 110 511, 0 118 087, 147 765 and in U.S. Pat. Nos. 4,618,572 and 4,656,123.

Reference is made to EP-A-193 389 as an example of the use of BAR couplers (bleach accelerator releasing coupler).

It may be advantageous to modify the effect of a photographically active group eliminated from a coupler by causing an intermolecular reaction of this group after its release with another group according to DE-A-35 06 805.

The eliminable residue may also be a ballast residue such that, on reaction with colour developer oxidation products, coupling products are obtained which are diffusible or have at least weak or restricted mobility (U.S. Pat. No. 4,420, 556).

The material may, in addition to couplers, contain various compounds which, for example, may liberate a development inhibitor, a development accelerator, a bleach accelerator, a developer, a silver halide solvent, a fogging agent or an anti-fogging agent, for example so-called DIR hydroquinones and other compounds as, for example, described in U.S. Pat. Nos. 4,636,546, 4,345,024, 4,684,604 and in DE-A-31 45 640, 25 15 213, 24 47 079 and in EP-A-198 438. These compounds fulfil the same function as the DIR, DAR or FAR couplers, except that they produce no coupling products.

High-molecular weight colour couplers are, for example, described in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284, U.S. Pat. No. 4,080,211. The high-molecular weight colour couplers are generally produced by polymerisation of ethylenically unsaturated monomeric colour couplers. They may, however, also be obtained by polyaddition or polycondensation.

The incorporation of couplers or other compounds into the silver halide emulsion layers may proceed by initially producing a solution, dispersion or emulsion of the compound concerned and then adding it to the pouring solution for the layer concerned. Selection of the appropriate solvent or dispersant depends on the particular solubility of the compound.

Methods for the introduction of compounds which are essentially insoluble in water by a grinding process are described, for example, in DE-A-26 09 741 and DE-A-26 09 742.

Hydrophobic compounds may also be introduced into the pouring solution by using high-boiling solvents, so-called oil formers. Corresponding methods are described, for example, in U.S. Pat. Nos. 2,322,027, 2,801,170, 2,801,171 and EP-A-0 043 037. Suitable oil formers for the magenta couplers according to the invention are described, for example, in DE-A-39 18 547.

Oligomers or polymers, so-called polymeric oil formers, may be used instead of high-boiling solvents.

The compounds may also be introduced into the pouring solution in the form of filled latices. Reference is, for example, made to DE-A-25 41 230, DE-A-25 41 274, DE-A-28 35 856, EP-A-0 014 921, EP-A-0 069 671, EP-A-0 130 115, U.S. Pat. No. 4,291,113.

The non-diffusible inclusion of anionic water-soluble compounds (for example dyes) may also proceed with the assistance of cationic polymers, so-called mordanting polymers.

Suitable oil formers are, for example, phthalic acid alkyl esters, phosphonic acid esters, phosphoric acid esters, citric acid esters, benzoic acid esters, amides, fatty acid esters, trimesic acid esters, alcohols, phenols, aniline derivatives and hydrocarbons.

Examples of suitable oil formers are dibutyl phthalate, dicyclohexyl phthalate, di-2-ethylhexyl phthalate, decyl phthalate, triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexylphenyl phosphate, 2-ethylhexyl benzoate, dodecyl benzoate, 2-ethylhexyl-p-hydroxybenzoate, diethyldodecanamide, N-tetradecylpyrrolidone, isostearyl alcohol, 2,4-di-t-amylphenol, dioctyl acelate, glycerol tributyrate, iso-stearyl lactate, trioctyl citrate, N,N-dibutyl-2-butoxy-5-t-octyl aniline, paraffin, dodecylbenzene and diisopropylnaphthalene.

Each of the differently sensitised photosensitive layers may consist of a single layer or may also comprise two or more partial layers of silver halide emulsion (DE-C-1 121 470). Here, red-sensitive silver halide emulsion layers are often located more closely to the film support than green-sensitive silver halide emulsion layers and these in turn are closer than blue-sensitive layers, wherein there is generally a non-photosensitive yellow filter layer between the green-sensitive layers and the blue-sensitive layers.

In cases of suitably low intrinsic sensitivity of the green or red-sensitive layers, different layer arrangements, dispensing with the yellow filter layer, may be selected. According to the invention, a preferred recording material is one which, on a light-reflective support, contains as the lowermost photosensitive layer a blue-sensitive layer with a yellow coupler, thereupon a green-sensitive layer with the combination according to the invention of a pyrazoloazole coupler and a light stabiliser and, as the uppermost photosensitive layer, a red-sensitive layer with a phenolic cyan coupler.

The non photosensitive interlayers generally located between layers of different spectral sensitivity may contain agents which prevent an undesirable diffusion of developer oxidation products from one photosensitive layer into another photosensitive layer with a different spectral sensitisation.

Suitable agents, which are also known as scavengers or EOP scavengers, are described in *Research Disclosure* 17 643 (December 1978), section VII, 17 842 (February 1979) and 18 726 (November 1979), page 650 and in EP-A-0 069 070, 0 098 072, 0 124 877, 0 125 522.

Examples of particularly suitable compounds are:

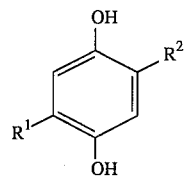

$R^1, R^2$
—$C_8H_{17}$—
—$C_{12}H_{25}$-a
—$C_6H_{13}$-t

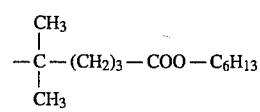

—$C_8H_{17}$-s
—$C_{15}H_{31}$

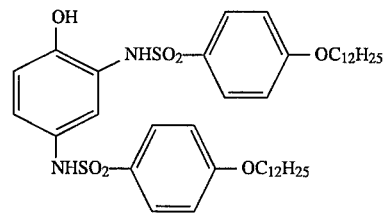

If there are several partial layers of the same spectral sensitisation, then they may differ in composition, particularly in terms of the type and quantity of silver halide grains. In general, the partial layer with the greater sensitivity will be located further from the support than the partial layer with lower sensitivity. Partial layers of the same spectral sensitisation may be adjacent to each other or may be separated by other layers, for example layers of different spectral sensitisation. Thus, for example, all high sensitivity and all low sensitivity layers may be grouped together each in a package of layers (DE-A-t19 58 709, DE-A-25 30 645, DE-A-26 22 922).

The photographic material may also contain UV light absorbing compounds, optical whiteners, spacers, filter dyes, formalin scavengers, light stabilisers, anti-oxidants, $D_{min}$ dyes, additives to improve stabilisation of dyes, couplers and whites and to reduce colour fogging, plasticisers (latices), biocides and others.

UV light absorbing compounds are intended on the one hand to protect the colour dyes from bleaching by high-UV daylight and on the other hand to absorb the UV light in daylight on exposure and so improve the colour reproduction of a film. Customarily, compounds of a differing structure are used for the two tasks. Examples are aryl-substituted benzotriazole compounds (U.S. Pat. No. 3,533,794), 4-thiazolidone compounds (U.S. Pat. No. 3,314,794 and 3,352, 681), benzophenone compounds (JP-A-2784/71), cinnamic acid ester compounds (U.S. Pat. No. 3,705,805 and 3,707, 375), butadiene compounds (U.S. Pat. No. 4,045,229) or benzoxazole compounds (U.S. Pat. No. 3,700,455).

Ultra-violet absorbing couplers (such as cyan couplers of the α-naphthol type) and ultra-violet absorbing polymers may also be used. These ultra-violet absorbents may be fixed into a specific layer by mordanting.

Filter dyes suitable for visible light include oxonol dyes, hemioxonol dyes, styryl dyes, merocyanine dyes, cyanine dyes and azo dyes. Of these dyes, oxonol dyes, hemioxonol dyes and merocyanine dyes are particularly advantageously used.

Suitable optical whiteners are, for example, described in *Research Disclosure* 17 643 (December 1978), section V, in U.S. Pat. Nos. 2,632,701, 3,269,840 and in GB-A-852,075 and 1,319,763.

Certain binder layers, in particular the layer furthest away from the support, but also occasionally interlayers, particularly if they constitute the layer furthest away from the support during manufacture, may contain photographically inert particles of an inorganic or organic nature, for example as flatting agents or spacers (DE-A-33 31 542, DE-A-34 24 893, *Research Disclosure* 17 643 (December 1978), section XVI).

The average particle diameter of the spacers is in particular in the range from 0.2 to 10 µm. The spacers are insoluble in water and may be soluble or insoluble in alkali, wherein alkali-soluble spacers are generally removed from the photographic material in the alkaline developing bath. Examples of suitable polymers are polymethyl methacrylate, copolymers of acrylic acid and methyl methacrylate together with hydroxypropylmethylcellulose hexahydrophthalate.

Additives to improve the stability of dyes, couplers and whites and to reduce colour fogging (*Research Disclosure* 17 643 (December 1978), section VII) may belong to the following classes of chemical substances: hydroquinones, 6-hydroxychromanes, 5-hydroxycoumaranes, spirochromanes, spiroindanes, p-alkoxyphenols, sterically hindered phenols, gallic acid derivatives, methylene dioxybenzenes, aminophenols, sterically hindered amines, derivatives with esterified or etherified phenolic hydroxyl groups, metal complexes.

Compounds having both a sterically hindered amine partial structure and a sterically hindered phenol partial structure in one molecule (U.S. Pat. No. 4,268,593) are particularly effective in preventing the degradation of yellow colour images as a consequence of the development of heat, moisture and light. In order to prevent the degradation of magenta colour images, in particular their degradation due to the effects of light, spiroindanes (JP-A-159 644/81) and chromanes which are substituted by hydroquinone diethers or monoethers (JP-A-89 835/80) are particularly effective.

Particularly suitable compounds are:

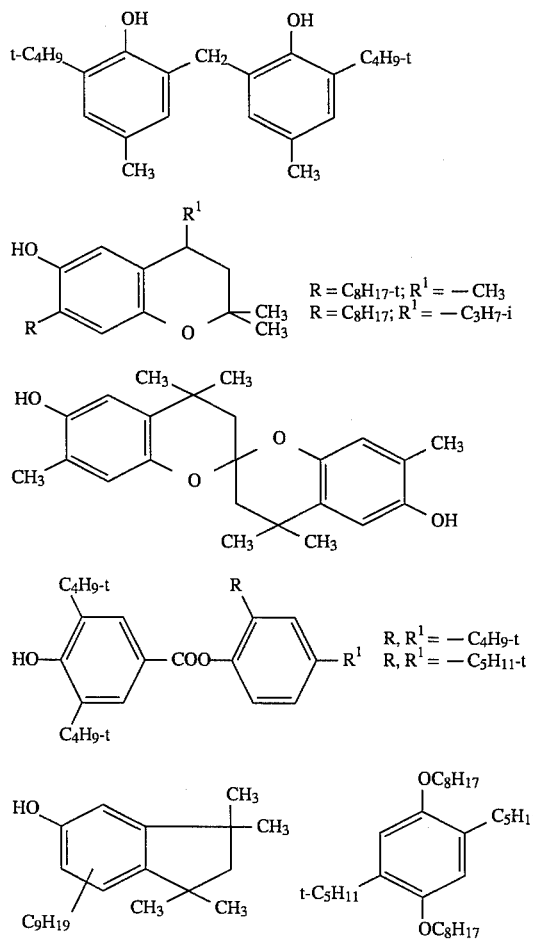

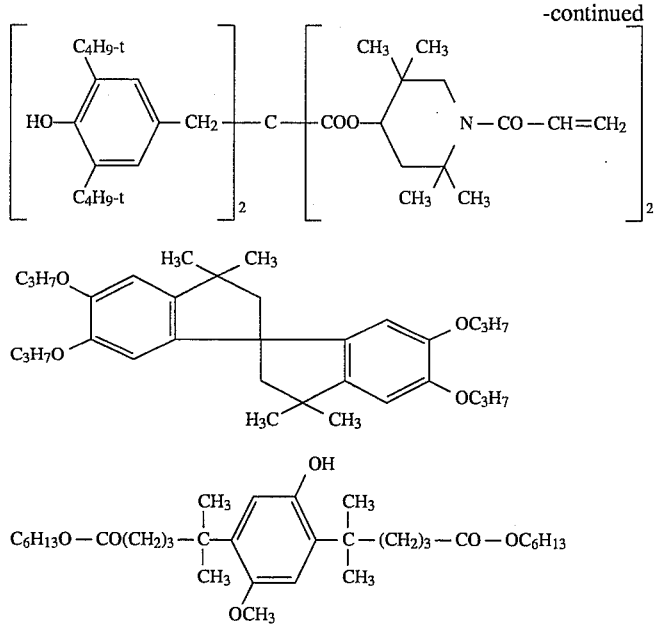

together with the compounds listed as EOP scavengers.

Colour photographic negative materials are customarily processed by developing, bleaching, fixing and rinsing or by developing, bleaching, fixing and stabilising without subsequent rinsing, wherein bleaching and fixing may be combined into a single processing stage. Colour developer compounds which may be used are all developer compounds having the ability to react, in the form of their oxidation product, with colour couplers to yield azomethine or indophenol dyes. Suitable colour developer compounds are aromatic compounds containing at least one primary amino group of the p-phenylenediamine type, for example N,N-dialkyl-p-phenylenediamines such as N,N-diethyl-p-phenylenediamine, 1-(N-ethyl-N-methanesulphoneamidoethyl)- 3-methyl-p-phenylenediamine, 1-(N-ethyl-N-hydroxyethyl)- 3-methyl-p-phenylenediamine and 1-(N-ethyl-N-methoxyethyl)- 3-methyl-p-phenylenediamine. Further usable colour developers are described for example in *J. Amer. Chem. Soc.* 73, 3106 (1951) and G. Haist, Modern *Photographic Processing*, 1979, John Wiley & Sons, New York, pages 545 et seq.

An acid stop bath or rinsing may follow after colour development.

Customarily, the material is bleached and fixed immediately after colour development. Bleaches which may be used are, for example, Fe(III) salts and Fe(III) complex salts such as ferricyanides, dichromates, water soluble cobalt complexes. Iron(III) complexes of aminopolycarboxylic acids are particularly preferred, in particular for example, complexes of ethylenediaminetetraacetic acid, propylenediaminetetraacetic acid, diethylenetriaminepentaacetic acid, nitrilotriacetic acid, iminodiacetic acid, N-hydroxyethylethylenediaminetriacetic acid, alkyliminodicarboxylic acids and of corresponding phosphonic acids. Also suitable as bleaches are persulphates and peroxides, for example hydrogen peroxide.

Rinsing usually follows the bleaching-fixing bath-or fixing bath, which is performed as countercurrent rinsing-or consists of several tanks with their own water supply.

Favourable results may be obtained by using a subsequent finishing bath which contains no or only little formaldehyde.

Rinsing may, however, be completely replaced with a stabilising bath, which is customarily performed countercurrently. If formaldehyde is added, this stabilising bath also performs the function of a finishing bath.

With colour reversal materials, there is an initial development with a black and white developer, the oxidation product of which is not capable of reacting with the colour couplers. There then follows a diffuse second exposure and then development with a colour developer, bleaching and fixing.

EXAMPLE

Individual yellow poured layers are produced for a colour photographic material suitable for rapid processing by applying 4 layers in the stated sequence to one side of a film support made of paper laminated on both sides with polyethylene.

The stated weights relate to 1 m², the corresponding quantity of AgNO$_3$ is stated for the quantity of silver halide applied.

Test material 1:

Comparison

Layer 1:

Substrate layer with 0.2 g gelatine

Layer 2:

Blue-sensitive silver halide emulsion prepared from 99.5 mol. % AgCl and 0.5 mol. % AgBr, average grain diameter 0.8 μm, corresponding to 0.46 g of AgNO$_3$ 0.5 g yellow coupler XY-1

0.2 g white coupler XW-1

0.5 g polyester prepared from adipic acid, 1,3-butanediol and 1,6-hexanediol

Layer 3:

1.1 g gelatine 0.06 g dioctylhydroquinone 0.06 g di-n-butyl phthalate

Layer 4:

0.9 g gelatine
0.3 g instant hardener, CAS registry n° 65411-60-1
The following compounds were used in layer 2.

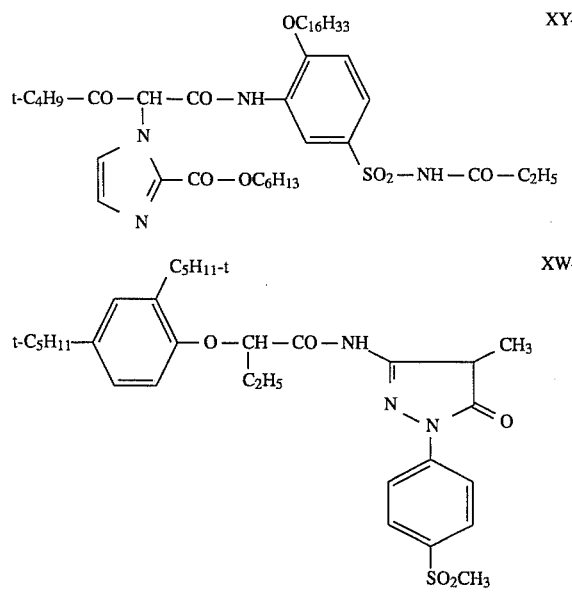

Test materials 2 to 5 (according to the invention) differ from test material 1 in that their layer 2 contains 0.5 g of one of the couplers 1, 2, 5 and 32 according to the invention instead of coupler XY-1.

The test materials obtained were exposed with blue light behind a grey wedge and processed as stated below. Stability against light and the action of heat was then determined.

| a) Colour developer - 45 s - 35° C. | |
|---|---|
| Triethanolamine | 9.0 g |
| N,N-diethylhydroxylamine | 6.0 g |
| Diethylene glycol | 0.05 g |
| 3-methyl-4-amino-N-ethyl-N-methane-sulphonamidoethyl-aniline sulphate | 6.0 g |
| Potassium sulphate | 0.2 g |
| Triethylene glycol | 0.05 g |
| Potassium carbonate | 22.0 g |
| Potassium hydroxide | 0.4 g |
| Ethylenediaminetetraacetic acid, disodium salt | 2.2 g |
| make up to 1,000 ml with water; | pH 9.2 |
| b) Bleaching/fixing bath - 45 s - 35° C. | |
| Ammonium thiosulphate | 75 g |
| Sodium hydrogen sulphite | 13.5 g |
| Ammonium acetate | 2.0 g |
| Ethylenediaminetetraacetic acid (iron-ammonium salt) | 57.0 g |
| 25% ammonia | 9.5 g |
| Acetic acid | 9.0 g |
| make up to 1,000 ml with water; | pH 5.5 |
| c) Rinsing - 2 min - 33° C. | |

The following result is obtained:

| Test material | $D_{max}$ | Light fading | Dark fading |
|---|---|---|---|
| 1 | 2.09 | −45% | −19% |
| 2 | 1.67 | −22% | ±0% |
| 3 | 1.29 | −33% | ±0% |

-continued

| Test material | $D_{max}$ | Light fading | Dark fading |
|---|---|---|---|
| 4 | 1.59 | −25% | ±0% |
| 5 | 1.36 | −40% | −5% |

Light fading is defined as the relative reduction in density at maximum density $D_{max}$ after exposure in a Xenotest device (9.6×10⁶ Luxh).

Dark fading is defined as the relative reduction in density under the action of heat without exposure to light at 90° C. for 8 days.

The results shows that the yellow dyes obtained from the yellow couplers according to the invention have superior dark fading stability, generally accompanied by more favourable light stability.

Test material 2 also has better absorption than test material 1, as may be seen from the $\lambda_{max}$ and half bandwidth values: while the absorption maximum is indeed at an 8 nm longer wavelength, the-half bandwidth is at a 7 nm shorter wavelength due to the steeper decrease on the long-wave side.

| Test material | $\lambda_{max}$ | $\lambda_{HBW}$ |
|---|---|---|
| 1 | 444 nm | 515 nm |
| 2 | 452 nm | 508 nm |

I claim:

1. A color photographic recording material comprising at least one photosensitive silver halide emulsion layer with a yellow coupler, wherein said yellow coupler is in said photosensitive layer or in an adjacent layer characterized in that the yellow coupler is of the formula I

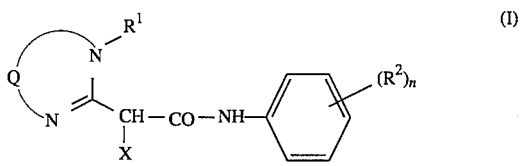

in which

Q means a residue to complete a 4-pyrimidone ring;

X means a residue which is eliminable on chromogenic development;

$R^1$ means alkyl with 1 to 6 C atoms;

$R^2$ means halogen, —$CF_3$, alkyl, aryl, alkoxy, aryloxy, alkylthio, arylthio, acylamino, sulphonamido, sulphuramido, carbamoyl, alkoxycarbonyl, sulphonyl, sulphamoyl or a heterocyclic residue, wherein two adjacent residues $R^2$ may complete a ring;

n means an integer from 1 to 4.

2. Recording material according to claim 1, wherein the residue represented by Q in formula I to complete a 4-pyrimidone ring is a group of the formula

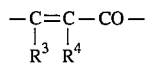

in which $R^3$ and $R^4$ mean a residue to complete a 5- to 7-membered ring, or $R^3$ and $R^4$ are the same or different and denote hydrogen, alkyl, aryl, alkoxy, —CN, acylamino, carbamoyl, alkoxycarbonyl, sulphonyl or a phosphorus ester group.

3. Recording material according to claim 2, characterised in that the eliminable residue represented by X in formula I is a 1,2,3- or 1,2,4-triazole residue.

4. Recording material according to claim 1, characterized in that it contains at least one blue-sensitive silver halide emulsion layer comprising a yellow coupler of the formula I and that it furthermore contains at least one green-sensitive silver halide emulsion layer comprising a magenta coupler represented by formulae VI or VII and at least one red-sensitive silver halide emulsion layer comprising a cyan coupler of the formula IV:

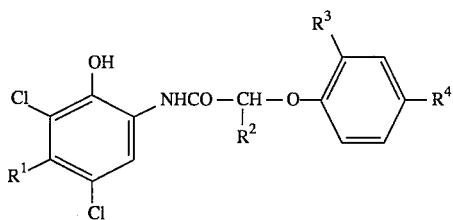

wherein
$R^1$ means alkyl with at least 2 C atoms
$R^2$, $R^3$ and $R^4$ are identical or different and mean alkyl;
Magenta coupler
and in formulas VI and VII:
X means H or a group which may be released under the conditions of color development;
$R^1$ means H, alkyl, aralkyl, aryl, alkoxy, aroxy, alkylthio, arylthio, amino, anilino, acylamino, cyano, alkoxycarbonyl, carbamoyl or sulphamoyl,
$R^2$ means tertiary alkyl.

* * * * *